US009168014B2

(12) United States Patent  
Beekman

(10) Patent No.: US 9,168,014 B2  
(45) Date of Patent: Oct. 27, 2015

(54) GAMMA RADIATION BREAST IMAGING APPARATUS

(71) Applicant: Milabs B.V., Utrecht (NL)

(72) Inventor: Frederik Johannes Beekman, Utrecht (NL)

(73) Assignee: Milabs B.V., Utrecht (NL)

( * ) Notice: Subject to any disclaimer, the term of this patent is extended or adjusted under 35 U.S.C. 154(b) by 206 days.

(21) Appl. No.: 14/044,019

(22) Filed: Oct. 2, 2013

(65) Prior Publication Data

US 2014/0093035 A1 Apr. 3, 2014

(30) Foreign Application Priority Data

Oct. 3, 2012 (NL) .................................. 2009566

(51) Int. Cl.
| | |
|---|---|
| *A61B 6/04* | (2006.01) |
| *A61B 6/00* | (2006.01) |
| *A61B 6/06* | (2006.01) |
| *G21K 1/02* | (2006.01) |
| *G01T 1/161* | (2006.01) |

(52) U.S. Cl.
CPC . *A61B 6/502* (2013.01); *A61B 6/06* (2013.01); *A61B 6/4291* (2013.01); *G21K 1/025* (2013.01); *A61B 6/0435* (2013.01); *G01T 1/161* (2013.01)

(58) Field of Classification Search
CPC ................................ G01T 1/161; A61B 6/502  
USPC ............................................................ 378/37  
See application file for complete search history.

(56) References Cited

U.S. PATENT DOCUMENTS

| 5,436,958 A | 7/1995 | Taylor |
| 2008/0116386 A1 | 5/2008 | Wagenaar et al. |

FOREIGN PATENT DOCUMENTS

| EP | 2073039 A1 | 6/2009 |
| WO | 2004006269 A1 | 1/2004 |
| WO | 2010014001 A2 | 2/2010 |

OTHER PUBLICATIONS

Search Report and Written Opinion for Priority Application NL 2009566 dated Oct. 3, 2012.

*Primary Examiner* — David Porta  
*Assistant Examiner* — Meenakshi Sahu  
(74) *Attorney, Agent, or Firm* — Hoffman & Baron, LLP

(57) ABSTRACT

A gamma radiation breast imaging apparatus, comprising an object positioning device, defining an imaging space and having as an intended insertion direction of the breast to be imaged, and a gamma camera positioned to image a volume in said imaging space. The gamma camera comprises a collimator with a first plurality of focused pinholes, the individual fields of view of the first pinholes defining a common central field of view having a geometrical center. The apparatus also has a gamma sensitive detector to receive images from the collimator. The first pinholes are provided non-symmetrically with respect to a first plane through said geometrical center that is perpendicular to the collimator and parallel to said intended insertion direction. Hereby, more angular information about the scanned volume can be obtained for the same detector size, in particular when combined with a similar opposite camera.

21 Claims, 8 Drawing Sheets

US 9,168,014 B2

GAMMA RADIATION BREAST IMAGING APPARATUS

CROSS REFERENCE TO RELATED APPLICATIONS

This application claims the benefit of Netherlands Application No. NL 2009566, filed Oct. 3, 2013, the contents of which are incorporated herein by reference.

FIELD OF THE INVENTION

The present invention relates to a gamma radiation imaging apparatus, in particular for breast imaging.

BACKGROUND OF THE INVENTION

Document WO2010/014001 discloses a breast scanner comprising an object positioning device, which comprises a frame supporting at least two positioning members—embodied as positioning plates—defining between them an imaging space for a breast to be imaged of a subject and allowing for insertion of the breast to be imaged in an intended insertion direction of the breast to be imaged, wherein at least one of the positioning members is movably mounted to said frame in a first direction substantially towards another positioning plate of the at least two positioning members, and wherein the positioning members are arranged to contact, e.g. compress, the breast when positioned between said positioning members. The known apparatus further comprises a gamma camera positioned to image a volume in the imaging space. The gamma camera comprises:
- a collimator provided with at least a first plurality of focused pinholes, each of the pinholes having an individual field of view, the individual fields of view of the first plurality of pinholes defining a common central field of view as the part of space seen by all of the first plurality of pinholes, and
- a gamma sensitive detector arranged to receive images from the collimator.

The collimator is positioned in a plane substantially parallel to one of the positioning members and is movable in said plane, preferably in orthogonal directions in said plane. The apparatus further comprises a collimator motion device arranged to controllably move the collimator in said plane.

Although this known apparatus has a relatively high accuracy and resolution, it suffers from the drawback that a relatively large fraction of the images are insufficiently accurate, for example showing an inaccurate location, or direction dependent blurring, of the tumor(s).

This can lead to an undesirably and unnecessarily high number of biopsies, tumor surgeries and breast amputations and also to a higher than necessary number of images being taken, which can cause discomfort or even pain to the patient, in particular to women of whom the breast is being imaged. In addition it can lead to undetected small tumors or parts of tumors in which case no, or insufficient amounts of, tumor tissue will be removed by a surgeon.

OBJECTS OF THE INVENTION

There is a persistent desire to increase the accuracy and resolution of a gamma radiation breast imaging apparatus, in order to improve as much as possible the detection of tumors and other defects, to thereby improve the health care.

It is an object of the present invention to provide apparatus which allows the accuracy in terms of resolution and noise properties to be further improved, thus allowing for more reliable imaging.

Another object of the invention is to provide an apparatus that has an increased versatility but preferably not at the cost of compactness.

Another object of the invention is to provide an apparatus that is convenient for the subject whereof the breast is imaged.

SUMMARY OF THE INVENTION

The invention achieves one or more of the above objects with a gamma radiation breast imaging apparatus, said apparatus comprising:
- a breast positioning device, which comprises a frame supporting a pair of breast positioning plates defining between them an imaging space for a breast to be imaged of a subject, wherein at least one of the breast positioning plates is movably mounted to said frame in a first direction substantially towards the other breast positioning plate allowing the breast positioning plates to compress the breast when positioned between said breast positioning plates, said apparatus further comprising:
- a gamma camera positioned to image a volume in said imaging space, wherein the gamma camera comprises:
    - a collimator having a first collimator plate part that is provided with at least a first plurality of focused pinholes, each of said first plurality of focused pinholes having an individual field of view, the individual fields of view of the first plurality of pinholes defining a common central field of view as the part of space seen by all of the first plurality of pinholes, and
    - a gamma sensitive detector arranged to receive images from the collimator, wherein the first collimator plate part of the collimator is positioned in a plane substantially parallel and adjacent to one of the breast positioning plates and is movable in said plane whilst the breast is compressed between the breast positioning plates, and wherein the apparatus further comprises a collimator motion device arranged to controllably move the collimator in said plane, preferably in two orthogonal directions, whilst the breast is compressed between the breast positioning plates, wherein the first plurality of focussed pinholes in said first collimator plate part is provided non-symmetrically when viewed in a coronal plane of the breast whilst the breast is compressed between the breast positioning plates.

In a practical embodiment the first plurality of focussed pinholes is provided non-symmetrically with respect to any plane that is perpendicular to the first plate part of the collimator and parallel to a practical insertion direction of the breast to be imaged, e.g. perpendicular to the torso of the human subject.

The inventive measure is in particular intended to mean that the range of imaging angles of said plurality of pinholes is provided non-symmetrically with respect to any said first plane.

Expressed in other words, the subset of said plurality of pinholes that is on one side of any such first plane is not a mirror image in said plane of the subset of pinholes of said plurality of pinholes that is on the other side of said plane. The same holds for the range of imaging angles of the subset of said plurality of pinholes that is on one side of any such first plane not being a mirror image of the range of imaging angles of the subset of said plurality of pinholes on the other side of said plane. Herein, random tolerances of an otherwise symmetrical design are not to be taken as providing this asymmetry. In particular, the range of acceptance angles, being represented by the extreme values in two directions, when viewed in a plane, is provided substantially non-symmetrically.

For example, if the range of acceptance angles as seen (and present) in a plane perpendicular to the collimator and perpendicular to the intended insertion direction runs from −30° to +30°, the range of acceptance angles and the corresponding plurality of pinholes is said to be provided symmetrically. If the range runs from −31° to +29°, is still is substantially symmetrical. "Substantially non-symmetrical" is understood here to mean a clear difference in absolute values, in particular at least 10° difference, such as from −60° to +50°, but also from −70° to −10°, and so on. Likewise, when an otherwise symmetrical plurality of pinholes were to be made asymmetrical by removing one or a few of the pinholes, then still the gist of the invention would not be applied, apart from the circumstance that detector surface usage would be inefficient. The present invention relates to basic asymmetry, in particular in the range of acceptance angles of the complete plurality of pinholes, or in other words of a non-symmetry in the range of the angles that the respective central lines of the individual cones of acceptance angles of each pinhole.

Thus, for example in a rectangular collimator, the pinholes of the first plurality are concentrated in, and directed toward a corner, of the camera/collimator. This leaves of course open the possibility to have an opposite part or corner of the collimator available for other purposes, such as plain shielding, or also to accommodate a second plurality of pinholes.

In this application the term a plurality of pinholes is to be taken as all pinholes in one and the same collimator that focus onto the same focus area/volume.

In some cases, there may be provided a set of pinholes in a first collimator as well as a set of pinholes in a second collimator, wherein (some or all) pinholes in both collimators focus onto one and the same focus area/volume. Such sets, or pluralities, of pinholes may be considered as one single composite set, but in the context of the present invention they will often still be considered separate sets. Not intended is of course the trivial case of considering a subset of such a complete plurality as a plurality, which can of course easily be taken as a non-symmetrical set. Note that it is also possible to provide a collimator with one or more additional pinholes that image, or focus onto, some different volume in the imaging space. The point is that there is in the collimator a plurality of pinholes that does focus on one and the same focus volume. Also note that "pinhole" here has its usual meaning, not being a simple through-hole as in parallel hole collimators, that do not focus.

A gamma imaging apparatus according to the invention offers the advantage that it is now easily possible to increase the angle over which angular image information can be obtained when imaging the breast. In the prior art, collimators with pinholes having a symmetrical central field of view ensured a certain angle for which such angular information could be obtained, when using a detector having a certain surface area. Of course, a trivial solution would be to increase that surface area indefinitely. However, according to this aspect of the present invention, better use is made of that surface area, by allowing a larger range of different angles to be imaged onto that surface area. After all, imaging from two opposite angles equal in magnitude, that are in line, i.e. along the same direction, does not add angular information, while imaging from two unequal angles does. Of course, the detector surface of the detector should be positioned such that the central field of view is substantially completely imaged onto that detector surface. Furthermore, alternatively or additionally, this aspect of the invention allows for an increased margin in selecting a suitable magnification factor for the imaging. Usually, one wants to collect angular information over a certain angle range, and also at a certain magnification factor. This places restraints on the gamma camera as a whole. By allowing the possibility to free up detector surface area, one can not only select a larger range of angles, but instead or also a larger magnification factor of the images, by increasing the distance between detector and collimator, without having to increase the detector surface area, as would have been the case in the prior art.

It is noted that the present invention may be considered as slightly counterintuitive. A single symmetrical collimator by itself provides more angular information for some specific detector area, than a single non-symmetrical collimator according to the invention. By providing an equal opposite collimator, the symmetrical design adds no angular information, as all directions/angles are already present in the first, single collimator. Contrarily, the non-symmetrical design now adds, and often almost doubles, angular information. This is a major advantage with respect to angular sampling for obtaining tomographic reconstructions when the system is moved from "left to right" in the plane for which those angles are considered. This does not follow from the cited document WO2010/014001, where FIG. 3 shows a collimator design that is non-symmetrical as seen in a sagittal plane, i.e. parallel to the intended insertion direction of the breast, and perpendicular to the collimator. This is however done to be able to image more deeply into the chest/breast tissue. Nothing at all is said about angular information, and no indication is given that more angular information can be obtained in the perpendicular coronal plane by applying the present invention. Furthermore, in this cited document, there is no need to image more to the side in the direction in the coronal plane, i.e. to the left or right when the subject is viewed from the front or back, because the cameras already scan all of the tissue. Thus, there is no need or suggestion to come to the present invention, that provides additional angular information in at least that coronal plane.

In the present invention, the intended insertion direction of the breast is understood to be a principal direction of the gamma camera, and coinciding with a main direction of actual insertion of the breast, assuming a slanted insertion that may sometimes take place is not intentional. As an everyday example, a garage, a pencil sharpener and a refrigerator all have an intended insertion direction which is clear, although a slanted insertion would still be possible. The intended insertion direction of the breast for imaging same is mainly, if not always, perpendicular to the coronal plane. Importantly, therefore, the mentioned plurality of focussed pinholes is advantageously provided non-symmetrically when viewed in a coronal plane of a human subject of which a breast is to be imaged. In other words, there is no visible symmetry in the collimator when viewed in a front view of the apparatus, i.e. no mirror symmetry in any of said first planes. Furthermore, the common central field of view is defined by the overlapping of all individual fields of view of a specific plurality of focused pinholes in a collimator. Another word for the common central field of view is therefore the focus volume. This focus volume is the part of the imaging space that is seen by all pinholes in that particular set/plurality of pinholes. As mentioned above, it is possible to have additional pinholes, such as those for imaging an additional volume outside and around the focus volume. Such pinholes are not considered part of the (first) plurality of (focused) pinholes.

The apparatus allows to make optimum use of the very high resolving power that is attainable with such a set-up with a pinhole collimator. In particular, this apparatus uses the strategy to bring pinhole(s) very close to the relevant tissues. Note that angular information is obtainable by moving the collimator with respect to the object, i.e. in a practical embodiment with respect to the positioning plate. The information is achieved from different parts of the detector, and will now provide at least the possibility to almost completely comprise 180° information, or at least to better estimate the desired complete 180° information.

In this invention "pinhole" comprises the concept of a hole in a wall, e.g. a rectangular plate or plate part, of a radiation opaque material, while there are cones leading to and from the pinhole. These cones, that may have a (preferably) circular, elliptical, square etc. cross-section, determine the opening angle of the pinhole, while the pinhole itself largely determines the sensitivity, through its cross-sectional area. In this respect, holes in e.g. parallel hole collimators, which are nothing more than channels in the collimator plate, are not treated as pinholes in this application. In the present application, providing different pinholes gives the possibility to adapt e.g. the sensitivity. By moving the collimator, such different pinholes may be positioned as desired with respect to the breast, for example with respect to a suspect part of the breast. In particular, at least part of the plurality of pinholes are focused towards a central field of view, or focus volume. This means that many pinholes have overlapping individual fields of view, i.e. they effectively (or collectively) "look" at the same volume, the focus volume, and image same onto the detector. This greatly increases the sensitivity and angular information, and hence the resolution. In this respect, focusing is to be understood as focusing in two dimensions, i.e. the pinholes are distributed in a plane, instead of along a line, while the central lines of the respective pinholes in such a plurality point substantially to a single point. The cones of directions for radiation that is able to penetrate then all overlap in a small, focus volume around said point. This point, the point where the central lines of the plurality of pinholes that focus onto the focus volume meet or at least the point that is on average closest to all those central lines, may be called the geometrical center of the focus volume.

It is furthermore noted that "perpendicular to the collimator" means either "perpendicular with respect to the local plane of pinholes in that collimator" or "perpendicular with respect to any positioning plate associated with said collimator". In practice, the collimators used for breast imaging cameras will almost always be at least locally flat or planar in the region of the pinholes, or embodied as a planar plate or with a planar plate part, in which case the concept of perpendicularity will be clear. In case of a collimator that is not flat or planar, the perpendicularity is to be taken locally, such as at or near a pinhole or otherwise indicated, or is to be taken with respect to the positioning plate along which a collimator is moveable. That positioning plate or plate part will in a practical embodiment (again) be flat or planar.

In embodiments, the individual field of view of each pinhole has a central line, in particular from said pinhole to said geometrical centre of the focus volume. Herein said first plurality of pinholes has a first pinhole of which the central line subtends a first angle with a perpendicular to the collimator which is the largest for said first plurality of pinholes, and a second pinhole that is furthest away from said first pinhole, wherein said first angle is substantially larger than a second angle between the central line of said second pinhole and a perpendicular to the collimator, in particular at the second pinhole. Herein, "substantially larger" is intended to mean "larger by more than just a production tolerance, and in particular at least 10° larger. Note that there might be a number of first pinholes equally far away from that plane, e.g. themselves in a parallel plane. Then an even more precise way to state this would be that the first pinhole is the pinhole furthest away from the focus volume, or its geometrical centre. Note furthermore in particular that in a symmetrical set-up, this feature does not hold, in that the first and second angles would be substantially the same.

An alternative way of saying that the first plurality of pinholes is provided non-symmetrically with respect to any (and all) first plane that is perpendicular to the collimator and parallel to said intended insertion direction of the breast is that the total field of view of said first plurality of pinholes, i.e. the combined fields of view, is asymmetrical with respect to any (and all) said first plane. In other words, an opportunity is created to use the detector surface, and correspondingly design a collimator, to obtain angular information for more different angles, instead of having a symmetrical design. In such a design, adding a similar second collimator on the opposite side of the breast cannot add angular information. Contrarily, in the present invention, adding such a similar second collimator can add angular information, but still with the same total detector surface. Thereto, it suffices to provide the second collimator as the mirror image of the first, mirrored in a plane right between the two collimators. For this alternative way, as for the invention as originally worded in claim 1 hereinabove, the inventive thought is to provide a way for gamma breast camera design in which pinholes at opposite ends of a particular plurality of focused pinholes in a (flat) collimator have fields of view at different angles with respect to that (flat) collimator. This means that a pinhole at a first end will have a certain (average or principal) angle for its field of view, with respect to the collimator, while a pinhole right at the opposite end of that plurality/collection of pinholes has a different angle. This means that one angle will be larger than the other, smaller one. Now, realising that a detector for such a camera accommodates on its surface area, and for a certain depth, a certain range of angles between that larger and smaller angle opposite, that same detector area and depth will allow a symmetrical collimator design for a maximum angle that is in between, and roughly the average of, the larger and smaller angle. Therefore, the latter design will have a smaller range of angular information.

In embodiments, said first angle is at least 45°, preferably at least 60°. The present invention allows such a large angle because it also allows economy and compactness for the detector, since the opposite side of the detector can be much smaller. In other words, a much larger part than half is available for the largest imaging angles. Still, other ranges for the first angle are possible, for example when large magnifications are required, or only a small detector is available.

In embodiments, said second angle is at least 30° smaller than the first angle. More in particular, the second angle is smaller than 20°, i.e. smaller than 20° absolute. By making the second angle relatively small, a lot of detector surface area may be freed for use in imaging at larger angles.

In particular embodiments, the first and second pinhole of the first plurality of pinholes are on the same side of the first plane through the geometrical center of the focus volume. This is an embodiment taking the inventive thought even further. For example, due to the fact that each pinhole will have an opening angle of its field of view, it is possible to configure the second pinhole such that the second line is at substantially the same angle as the opening angle of its field of view. In other words, the extreme part of the field of view is at a right angle with the collimator, and thus with the object. Although sensitivity is then of course minimal, one still has angular data for this extreme situation, in theory a single ray for the right angle.

In other embodiments, the second angle is substantially zero. This allows a full-sensitivity measurement of the right angle situation, while freeing almost half the detector surface area for larger angles at the extreme end, with a simple geometrical set-up as a bonus. It is therefore a suitable design for many situations. One could view the collimator in this embodiment as a "half-collimator", though strictly speaking the centre part is still present.

In advantageous embodiments, at least the first plurality of focussed pinholes is furthermore provided non-symmetrically with respect to any second plane that is perpendicular to the collimator and perpendicular to the intended insertion direction of the breast. In particular, the first plurality of focussed pinholes is provided non-symmetrically with respect to the (or any) coronal plane as well as with respect to the (or any) sagittal plane. Even more in particular, this set-up of the plurality of pinholes is present in each collimator, i.e. both an upper and a lower collimator, for each of the plates. With these embodiments, these is an additional gain in angular information, as the increase according to the inventive thought of claim 1 is now applied in all directions. It is again noted that, although FIG. 3 of document WO2010/014001 discloses the separate measure per se, there is no realisation of its advantage with respect to gain in angular information, and certainly not in the coronal plane, for which there is no need or hint in WO2010/014001 to apply said feature. It is expressly noted that any and all embodiments and advantages mentioned herein with respect to the asymmetry with respect to any first plane is also deemed to hold for asymmetry in the opposite direction, such as in particular not only coronal, but also sagittal.

In embodiments, the collimator comprises a rectangular collimator plate or plate part of radiation opaque material, in which there is provided said first plurality in a first corner of said plate. This can be seen as a design possibility (or design consequence) of the invention, due to the asymmetrical layout. Having the plurality of pinholes in a layout with asymmetry in two opposite directions allows an increase in angular information, as explained above. Advantageously, they are provided in a corner of the collimator plate or plate part. An advantage is furthermore that more space or room around the collimator is created to accommodate a breast to be imaged. Note that the detector will extend, with respect to the collimator, in the direction along the acceptance angles, starting from the corner with the plurality of pinholes. In the other direction, there need not be any part of the apparatus. Thus, the corner with the first plurality of pinholes can be brought close to the object, while the object can extend in the part of the space extending in said other direction. Of course, if the object to be imaged is substantially flat and much larger, this will hardly bring any advantages, but in most cases, such as human patients, this is a much more irregular shape, and the object, e.g. breast, may be approached more closely by the present apparatus and its collimator.

Advantageously, the collimator further comprises an additional second plurality of pinholes, and the second plurality is provided at a neighbouring corner to said first corner with said first plurality of pinholes and is substantially a mirror image of said first plurality. The mirroring is done with respect to a suitable plane, such as a plane of symmetry for the collimator plate, or at least a plane in the middle between the two sets of pinholes. By providing such a set-up, only one breast at a time needs to be received and possibly compressed between positioning members, e.g. positioning plates, while there can be additional space for e.g. an arm of the subject.

In embodiments, the apparatus comprises two of said gamma cameras, preferably each of the design discussed herein, each associated with one of two breast positioning plates or similar members of the apparatus. By having two gamma cameras, in practice on two sides of the imaging space, one obtains up to at most twice as much angular information, thus at least more complete data. Importantly, it is such an embodiment that actually allows to make optimum use of the advantageous possibilities provided by the non-symmetrical collimator according to the invention. Note that it is possible to provide a gamma camera with a non-symmetrical collimator and opposite thereof an additional gamma camera with a symmetrical collimator, such as for increased sensitivity around the right angle.

In embodiments of the apparatus, at least one breast positioning member comprises a first breast positioning plate part, preferably a planar first positioning plate part, and a second positioning plate part that adjoins the first breast positioning plate part and extends at a non-zero angle, preferably perpendicular, to said first breast positioning plate part.

In a further development the collimator associated with said at least one breast positioning member and a collimator motion device are configured to move the collimator along said first breast positioning plate part and along said second positioning plate part.

Preferably the frame of the apparatus is embodied to support said breast positioning member such that said first breast positioning plate part is oriented to support the breast laterally, e.g. at an incline, and the second positioning plate part is oriented to support the subject in the region of the armpit, preferably to support a portion of the upper arm adjacent the armpit of the subject.

In an embodiment the frame of the apparatus is embodied to support said breast positioning member such that—when seen in frontal view of the subject—the first breast positioning plate part is oriented at an incline from said armpit towards a center of the torso and the second positioning plate part is oriented at an incline from the armpit downward and outward. This embodiment with at least one positioning member that comprises a first breast positioning plate part, preferably a planar first positioning plate part, and a second positioning plate part that adjoins the first breast positioning plate part and extends at a non-zero angle, preferably perpendicular, to said first breast positioning plate part, allows—in conjunction with a suitable gamma camera—for imaging of not only a breast but also neighbouring tissue, in particular axillar tissue, such as lymph nodes and associated tissue of the armpit, which tissue is also very relevant in scans for e.g. breast cancer.

In an embodiment, at least a lower breast positioning member is embodied such as to allow scanning of the breast and of the associated armpit. In an embodiment the member has a second positioning plate part that extends generally outwardly and downwardly from an armpit apex of the member, e.g. away from another plate part of the member. Often, simply a right angle between the two positioning plate parts, e.g. each of generally planar shape, will do, in some cases with a rounded edge at the apex between the two plate parts for comfort of the subject. In other cases, it is also possible to allow a different angle between adjoining positioning plate parts, in particular if the associated collimator is adapted to follow the plane of the second positioning plate part by either being tiltable or by having a side in conformity with the second positioning plate part.

In use, a subject of which a breast is to be scanned could e.g. lay her arm over a second plate part of a lower breast positioning member, with an upper second positioning member moved upwards or even away to facilitate placement of the breast against the first plate part of the lower positioning member. The armpit then rests against or is in the vicinity of the join between the first and second positioning plate parts, the arm being at e.g. a right angle with respect to the body— e.g. with the subject standing—, which is rather comfortable. The relevant tissue can then be scanned by moving the collimator along each of the plate parts, preferably in succession. Herein, a very important advantage of the present invention of claim 1 is that this collimator design provides the possibility to have the focus area be positioned at least partly to the side of the collimator, i.e. outwardly from the space between the two collimator plates or two first collimator plate parts when in a position to scan a breast. This makes the scanning much easier, and much more comfortable. Contrarily, in prior art collimators, the collimator extends beyond the focus area on all sides, allowing imaging of an armpit only with the arm stretched out parallel to the body, which is rather uncomfortable. Of course, this possibility of more easily scanning an armpit comes as a bonus to scanning of the breast.

In particular, the collimator may comprise a substantially flat or planar first collimator plate part and a substantially flat or planar second collimator plate joining the first collimator plate part and extending at a non-zero angle, preferably a substantially downward and perpendicular angle, to the first collimator plate part. Preferably said collimator, e.g. said second collimator plate part, comprises a third plurality of pinholes having a separate central field of view, distinct from the central field of view afforded by the first plurality and, when present, by the second plurality of pinholes of the collimator. While it is possible, as described further above, to use the a single collimator plate with a first plurality of pinholes for imaging both breast tissue and axillary tissue, it considered advantageous to use a dedicated and distinct set or plurality of pinholes for imaging said axillary tissue, preferably said additional set of axillary tissue imaging pinholes being positioned at or near a join of a first collimator plate part and a second collimator plate part, e.g. with at least one pinhole of said third plurality in said second collimator plate. One is then free to select the number of pinholes, their focus area and so on for optimum axillary imaging.

In embodiments, most importantly when the collimator has multiple pluralities of focussed pinholes, the apparatus further may comprise one or more pinhole shutter devices that are each configured to selectively open and close at least one of the pluralities of pinholes. By selectively opening and closing a plurality of pinholes, specific imaging onto the detector can be selected, thereby preventing noise from non-focused radiation, but also providing the possibility to use parts of the detector area for more than one plurality of pinholes. The later could easily arise for pinholes on different collimator plate parts. Another, very particular use of the pinhole shutter devices could be to emulate moving of the gamma camera with respect to the object to be imaged. By selectively opening only suitable shaped pinholes, one can emulate the movement of the (central) field of view through the subject, without actually having to move either the collimator/gamma camera as a whole or the subject.

In embodiments, the detector is arranged at an acute non-zero angle with the collimator or with a collimator plate part thereof, e.g. with the collimator having perpendicular first and second collimator plate parts and the detector at an incline with respect to each of said plate parts. This further allows to increase the range of angles, as such tilted arrangement of the detector with respect to the collimator—compared to the common parallel arrangement to a plate collimator—mimics increasing the surface area thereof. In the extreme case of the detector and the (extension of) the collimator touching, one has almost a flat measuring set-up. If the detector is supported so as to be tiltable with respect to the collimator, e.g. by a detector tilting device of the gamma camera, one can e.g. use a one-piece flat detector, which is easy to produce and versatile, with good use of all its surface area. This would not be possible in the prior art, as a symmetrical detector would mean a detector that is flat throughout, thus also in the middle. This in turn means no tilting, and thus no touching of the extension of the collimator. And though it would be possible to provide a two-part detector surface, with a bend in the middle to allow said touching with the extension of the collimator, such bend is highly undesirable, and certainly not useful for measuring.

In embodiments the collimator is selectively moveable horizontally and vertically, in each case along its associated positioning plate part when present. This allows to image the breast, and/or other tissue, to be imaged under different angles.

In an important embodiment, the breast positioning device is tiltable, such that at least the breast positioning members or plates are or can be arranged at an approximately 45° angle with respect to the vertical, e.g. when the subject is standing or sitting. Thereto, the apparatus may comprise a frame with a pivot mechanism, e.g. with horizontal pivot axis, with respect to which the one or more gamma cameras and positioning members are tiltable. This allows insertion, and imaging, of the tissue of (part of the) breast, and possibly of the armpit and tissue in-between. Of course, one may allow for adjustability of the tilting so that the exact angle with respect to the vertical may be dependent on the body of the subject.

In a suitable embodiment of the apparatus of the present invention the position of the members between which the breast is positioned is exactly known and the distance between pinholes and a breast lesion may be made very small, e.g. down to the thickness of one of the positioning plates, and of course the collimator and the desired distance, if any, between the collimator and the detector. The apparatus of the present invention may use this minimal distance by allowing to scan parallel to the very positioning plate that may contact the breast, or even compresses the breast to a certain degree. This small distance is a great advantage for image quality.

In embodiments, the collimator is substantially contiguous to one of the positioning members or plates. Herein, this is understood as the distance between the relevant positioning plate and the collimator being smaller than 3 cm, preferably substantially zero, i.e. sliding contact between the plate and the collimator, apart from a little play to allow the movement.

Note that "movable in a plane" is intended to mean that the collimator is preferably able to move in at least two different, e.g. orthogonal, directions in said plane.

As discussed it is not necessary for the detector to be parallel to the collimator or a collimator plate part. Although a non-parallel arrangement might lead to a somewhat distorted image, this distortion is relatively easily corrected by suitable image processing software, while this allows a favourable positioning of the pinhole(s) of the collimator and of the detector with respect to the object. The central line of the pinhole will often be at a sharp angle with respect to the plate to allow full imaging.

At least one of the positioning members, e.g. one of a pair of positioning plates, is movable in the frame, in a direction substantially towards another of the at least two members or plates, such as perpendicular to the plate if the plates are maintained in parallel orientation throughout. This e.g. allows the object to be imaged, in particular a woman's breast, to be compressed. This makes the object to be imaged thinner, and the obtained images more unambiguous. In this application, the object to be imaged will be taken to be a woman's breast, although other objects or body parts, in particular those which are compressible, are also possible. In principle, contacting or compressing the breast brings significant advantages as to resolution of the gamma radiation imaging.

In embodiments, the apparatus comprises a further or second gamma camera, having a further collimator and a further gamma sensitive detector, wherein the first gamma camera and the further or second gamma camera are arranged on opposite sides of the imaging space. In certain embodiments, the gamma cameras are of a similar or even identical type, which makes evaluation of their images easier and production more efficient.

In special embodiments, the gamma camera(s) is (are each) a SPECT type camera. In particular, the gamma camera(s) is/are arranged to image very high energy photons (e.g. 511 keV) that can normally only be detected by coincidence PET systems. Imaging in combination with a collimator gives a lower sensitivity than coincidence PET cameras, but an even increased resolution when pinhole opening cones are narrow, which also allows imaging of very high energy photons. It is however also possible to provide two different gamma cameras, such as with different detectors, that have different detection efficiencies, e.g. for different energy, or that have different pinholes and so on.

In practice, a collimator (and possibly also detector) motion device is arranged for controllably moving the collimator (and possibly detector) in a plane parallel to the respective positioning member or positioning plate. This may e.g. be embodied such that the collimator motion device is adapted for motion along two orthogonal axes in said plane, or along a regular scanning path, e.g. a serpentine or zig-zag path, or a completely random path and so on. The collimator motion device may be computer-controlled.

In special embodiments, the collimator of a further or second gamma camera is positioned in a further plane substantially parallel to another positioning member or plate of the at least two positioning members and is movable in said further plane, wherein the plane and the further plane are arranged to subtend a non-zero angle. This allows the members or plates to be non-parallel, which provides the advantage of allowing contacting or compressing the breast in a different way than with parallel members. The positioning members may be provided in such an angle or shape that they are as much as possible adapted to the shape of the breast, and contact it as little as possible, or at least as evenly as possible. This provides less discomfort to the woman. The operation of the or each collimator motion device may be adapted to this angular orientation of said planes, e.g. by scanning during a correspondingly longer time at a location where the tissue thickness between the positioning members is greater than in thinner regions. Possibly the angle between the positioning members plates is adjustable. Note that the collimator may thus also be positionable, i.e. under that adjustable angle.

In embodiments, the gamma camera as a whole is movable in a plane substantially parallel to the positioning member or positioning plate, and the collimator motion device is arranged to controllably move the gamma camera in said plane. One could say that in this case the detector, and possibly other parts of the gamma camera, are coupled or fastened to the collimator, and they are moved together with the collimator. By moving the camera or each of the cameras as a whole, i.e. keeping the distance between detector and collimator fixed, calculations with respect to the obtained images are relatively easy. It is however also possible to arrange the collimator and detector for one or more gamma cameras such that the distance between them is adjustable, enabling an adaptive zoom or magnification effect.

The moving of the collimator(s) or gamma camera(s) as a whole may be along a predetermined path, such as a zigzag path for scanning the whole breast. The collimator motion device may be arranged accordingly, such as by providing an accordingly programmed computer in the motion device.

In embodiments, the apparatus is adapted or programmed to image the object to be imaged in a fast mode, wherein only a collimator is moved in the plane, or each of the collimators is moved. This allows a very fast scan, because only the collimator has to be displaced and not the whole camera, as is the case in the prior art. A collimator is of course much lighter than the collimator plus the rest of a gamma camera, but since the present invention also has a very small object-to-pinhole distance, the sensitivity can be very high, all of which accounts for the high possible scan speeds.

A particular advantage of the invention is that it allows the recording of dynamic images. In particular, tracers like $^{99m}$Tc-MIBI can be applied to e.g. suspect or tumor tissue, and then dynamically imaged to study the changes to the concentration of the tracer in the tissue. This is a helpful tool in studying phenomena like tumor response to chemotherapy.

Note that the apparatus of the present invention may also be adapted or programmed to image the object to be imaged in a fast mode by moving a gamma camera (or the gamma cameras) as a whole. In each case, it is possible to provide dynamic images, or time-dependent images of the object.

Preferably, at least one set or plurality of pinholes with an opening top angle of at most 40°, and preferably at most 25°, is provided, which give good, to excellent, imaging properties for high energy photons. In the case of clustered pinholes, such as described in EP2073039 by the present applicant, and incorporated by reference in its entirety, it is the total top angle per cluster, with individual top angles correspondingly smaller. For example, the MILabs VECTor has a 2×2 pinhole per cluster set-up, with a total top angle per cluster of about 32°, with individual pinholes having a top angle of about 16°.

In some embodiments, at least one pinhole comprises a cross-slit pinhole. This is meant to indicate a pinhole that does not consist of a simple hole in the collimator plate, with cones leading to and from it, but the combination of two crossed, i.e. non-parallel, slits in two parallel collimator plates. This also has the effect of a pinhole. Note that the slits in the collimator plates should have a profile of a pyramid, to ensure an opening angle etc.

In embodiments, at least one cross-slit pinhole comprises adjustable crossed slits. This allows variation of e.g. the width of the pinholes, and thus the sensitivity, by moving of the two collimator plates with respect to each other. It is also possible to shift the mutual position of the pinholes and so on.

In particular embodiments, the apparatus further comprises a marker system, that is arranged to mark the object, e.g. breast, during imaging. This allows more reliable re-imaging of the object in a subsequent imaging, either with the same apparatus or with a different apparatus, such as an X-ray camera. Marking can be done with any desired kind of marker, but preferably relates to visible markers for ease of use. For details, reference is made to WO2010/014001, in particular pages 9 and 10, herein incorporated by reference.

The present invention also relates to a gamma radiation imaging apparatus, said apparatus comprising:
   an object positioning device, which comprises a frame supporting at least two positioning members defining between them an imaging space for a breast to be imaged of a subject and allowing for insertion of the breast to be imaged in an intended insertion direction of the breast to be imaged, wherein at least one of the positioning members is movably mounted to said frame in a first direction substantially towards another positioning plate of the at least two positioning members, and wherein the positioning members are arranged to contact, e.g. compress, the breast when positioned between said positioning members,
said apparatus further comprising:
   a gamma camera positioned to image a volume in said imaging space, wherein the gamma camera comprises:
      a collimator, and
      a gamma sensitive detector arranged to receive images from the collimator,
wherein at least one positioning member comprises a first positioning plate part, preferably a planar first positioning plate part, and a second positioning plate part that adjoins the first positioning plate part and extends at a non-zero angle, preferably perpendicular, to said first positioning plate part.

In an embodiment the collimator associated with said at least one positioning member and a collimator motion device are configured to move the collimator along said first positioning plate part and along said second positioning plate part.

In an embodiment the frame of the apparatus is embodied to support said positioning member such that said first positioning plate part is oriented to support the breast laterally and the second positioning plate part is oriented to support the subject in the region of the armpit, preferably to support a portion of the upper arm adjacent the armpit of the subject. In an embodiment the frame of the apparatus is embodied to support said positioning member such that—when seen in frontal view of the subject—the first positioning plate part is oriented at an incline from said armpit towards a center of the torso and the second positioning plate part is oriented at an incline from the armpit downward and outward.

In an embodiment the collimator comprises a first collimator plate part, preferably a planar collimator plate part, and a second collimator plate that adjoins the first collimator plate part and extends at a non-zero angle, preferably perpendicular, to said first collimator plate part at a non-zero angle, preferably the first collimator plate part being arranged in the frame to extend along a lateral side, top, or bottom of the breast to be imaged and the second collimator plate part being arranged in the frame to extend either along the chest of the subject or along, e.g. underneath, an upper arm portion of the subject.

In an embodiment the collimator comprises a third plurality of pinholes each of the pinholes having an individual field of view, the individual fields of view of the third plurality of pinholes defining a common third central field of view as the part of space seen by all of the third plurality of pinholes, said third central field of view being distinct from said central field of view of said first and possibly second plurality of pinholes, preferably said third central view of view corresponding to an armpit region of the subject.

In an embodiment the third plurality of pinholes is provided in the region where the second collimator plate part adjoins the first collimator plate part.

In an embodiment the first collimator plate part is parallel to the first positioning plate part and wherein the second collimator plate part is parallel to the second positioning plate part, preferably the adjoining plate parts extending perpendicular to one another.

In an embodiment the collimator motion device is adapted to at least allow for displacement of the collimator along an axis perpendicular to the second positioning plate part, preferably with the first collimator plate part moving closely along the first positioning plate part, and to at least allow for displacement of the collimator along an axis perpendicular to the first positioning plate part, preferably with the second collimator plate part moving closely along the second positioning plate part.

In an embodiment the detector is arranged at an angle relative to both the first and the second collimator plate part, possibly an adjustable angle by means of detector angle adjuster.

The present invention also relates to a gamma radiation imaging apparatus, said apparatus comprising:
   an object positioning device, which comprises a frame supporting at least two positioning members defining between them an imaging space for a breast to be imaged of a subject and allowing for insertion of the breast to be imaged in an intended insertion direction of the breast to be imaged, wherein at least one of the positioning members is movably mounted to said frame in a first direction substantially towards another positioning plate of the at least two positioning members, and wherein the positioning members are arranged to contact, e.g. compress, the breast when positioned between said positioning members,
said apparatus further comprising:
   a gamma camera positioned to image a volume in said imaging space, wherein the gamma camera comprises:
      a collimator, and
      a gamma sensitive detector arranged to receive images from the collimator,
wherein the collimator comprises a first collimator plate part, preferably a planar collimator plate part, and a second collimator plate that adjoins the first collimator plate part and extends at a non-zero angle, preferably perpendicular, to said first collimator plate part at a non-zero angle, preferably the first collimator plate part being arranged in the frame to extend along a lateral side, top, or bottom of the breast to be imaged and the second collimator plate part being arranged in the frame to extend either along the chest of the subject or along, e.g. underneath, an upper arm portion of the subject.

The present invention also relates to a gamma radiation breast imaging camera as disclosed herein, e.g. as specified in one or more of the appended claims.

The present invention also relates to an assembly of a gamma radiation breast imaging camera and at least one positioning member as disclosed herein, e.g. as specified in one or more of the appended claims.

The present invention also relates to a method for imaging a breast by means of a gamma radiation imaging apparatus, camera, or assembly of camera and positioning member(s), as disclosed herein.

The subject may be sitting during imaging or standing, or even lying on a table with the chest down so as to have the breast in pendulant state. One may envisage the latter version with the table having an opening therein for the breast and the arrangement of positioning members and camera or cameras below the table. One may envisage that the breast is kept in pendulant, non or hardly compressed state during the imaging. For example the positioning device is first operated to slightly compress the breast so as to position it, and then the device is operated to reduce or remove compression so that the breast in freely or merely lightly positioned pendulant state during imaging.

One can also envisage an embodiment wherein the subjects torso is leaned forward onto a chest support, e.g. with an opening therein as described above in relation to the table.

The invention as described hereinabove will now be explained in more detail with reference to non-limiting exemplary embodiments, reference being made to the appended drawings.

BRIEF DESCRIPTION OF THE DRAWINGS

FIGS. 7-9.

DETAILED DESCRIPTION OF EMBODIMENTS

Figure 1:
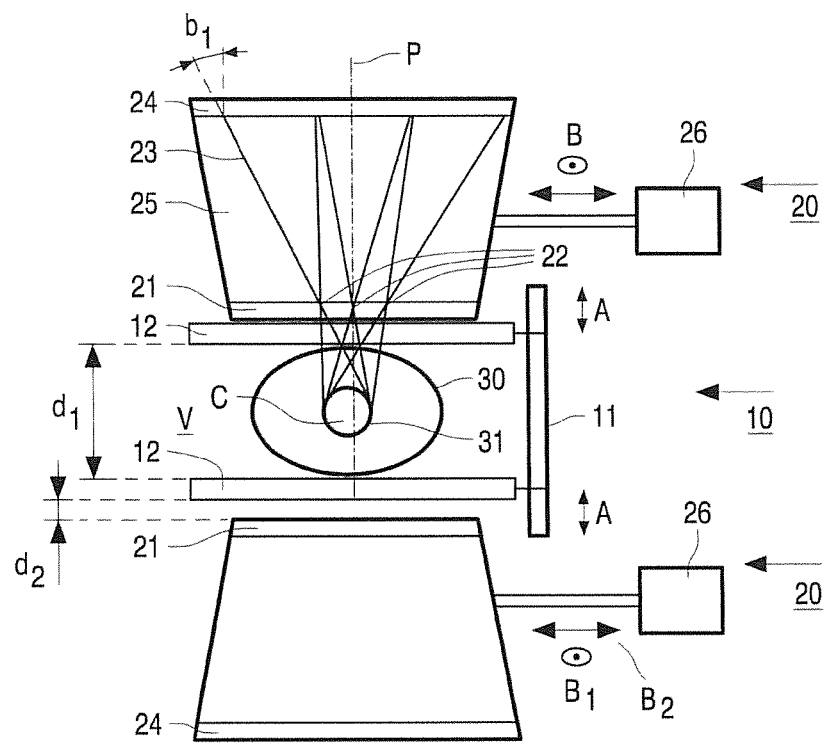
FIG. 1 shows diagrammatically an apparatus according to the prior art.

FIG. 1 shows diagrammatically an apparatus according to the prior art, in particular according to the cited document WO2010/014001, with a breast 30, a positioning device 10, and two gamma cameras 20-1, 20-2 generally above and below the breast to be imaged.

It is noted that one or more parts present in this prior art apparatus may, and preferably are, also present in the apparatus according to the invention, albeit sometimes in a modified form. Thus, for reasons of avoiding repetition, it is hereby assumed that a part or parts indicated in FIG. 1 or discussed with reference to FIG. 1 but not show or discussed with reference to all the other figures may be present therein as well.

Now turning to FIG. 1. The object or breast positioning device 10 comprises a frame 11, e.g. a frame to be placed on the floor of an exam room. The frame 11 supports two positioning members, embodied as plates 12, as is shown in a mutually parallel orientation, as is shown and practically simple in horizontal orientation. At least one or the plates 12, here each of the pair of parallel plates 12, is movable in the direction of arrows A, e.g. manually or by means of a positioning member motion device. Such device can comprises an electric motor or other motorized drive (not indicated). The plate motion of each plate 12 allows for adjustment of the distance between the plates 12 and therefore of a dimension of imaging space V wherein the breast 30 is accommodated for imaging.

Note that in an embodiment only one positioning plate 12 may be adjustable relative to the frame 11, with the other plate 12 being stationary mounted on the frame 11, e.g. a lower plate 12 being adjustable in position relative to a stationary mounted upper plate 12. Having a fixed upper positioning plate 20 avoids any risk of unexpectedly falling down thereof and of any part on top of it, such as a gamma camera, thus avoiding the risk of crushing a patient's body part.

Furthermore, one or both plates 12 may be rotatably or slidably mounted to the frame 11, for instance allowing one or both plates 12 to be moved to a side, away from the effective imaging space V, in order to further open the imaging space V and facilitate introduction and removal of the breast 30 in the imaging space V.

Each of the plates 12 or other version of the positioning member 12 is preferably made of a rigid material, e.g. a body contact compatible material.

Each of the plates 12 near a gamma camera 20 is made of a material that is sufficiently transparent to gamma radiation.

In a dual mode version of the apparatus additionally an X-ray source is provided as well as a detector adapted for X-ray, e.g. a detector capable of handling both gamma and X-ray radiation. Preferably then, each plate 12 or other version of positioning member is also transparent to X-rays to allow the use of the X-ray device.

Furthermore, advantageously one or more of the plates 12 is at least partly optically transparent to allow a visual check, e.g. by means of an optical camera of the apparatus when provided. Examples of useful materials for the one or more plates 12 are glass or preferably plastics such as Plexiglas or polycarbonate.

Each of the plates 12 may have a thickness that could be as small as one or a few millimeters, e.g. between 1 and 6 millimeters.

An imaging space V is defined between the plates 12. Due to the mobile support of one or more of the plates 12 relative to the frame 11 the effective thickness or height of the imaging space V is adjustable, here indicated by the parameter d1. In practical situation the distance d1 between the plates 12 will depend on the size of the breast 30 and on the degree of compression of the breast 30.

In case only one plate 12 and one gamma camera 20 are provided, the space V is defined as the space on the side of the plate 12 facing away from the gamma camera 20, and having a thickness of between 1 and 20 cm.

In the imaging space V, a breast 30 is present, as the object to be imaged. As indicated and preferred, the breast 30 is hardly compressed, although adjustment of the spacing between the plates 12 may bring about a desired degree of compression to decrease the thickness of the breast in perpendicular direction which generally enhances the imaging.

To the side of at least one, here each, plate 12 that is remote from the imaging space V a gamma camera 20 is arranged, preferably supported also by the frame 11 of the apparatus.

The gamma cameras 20 are by way of example shown to be of identical type, although in some embodiments this need not be the case, allowing e.g. different pinhole arrangements to be used in each camera 20. Here, the cameras 20 are identical and mirrored in a plane between the two cameras.

Each gamma camera 20 comprises a collimator 21, here embodied with a single collimator plate 21, the collimator being provided with pinholes 22, defining beams 23 that point toward a detector 24 of the camera 20.

The collimator 21 and the detector 24 of each camera 20 are arranged in a housing 25, which is preferably but not necessarily radio-opaque.

Alternatively, and as is more common in the field, one could say that the pinholes 22 in the collimator 21 define acceptance angles in the space imaged by them, which angles correspond, on the other side of the pinholes 22, with said beams 23.

A collimator motion device is generally and diagrammatically indicated by 26, and is able to move the collimator, here the housing 25 with the collimator 21 and the detector 24, in a plane in the direction of the arrows $B_1$ and $B_2$, pointing horizontally in and perpendicular to the plane of the paper, and from left to right, respectively. $B_1$ also indicates a practical and intended direction of inserting the breast 30 into the imaging space V between the plates 12.

The collimator plate 21 comprises a first plurality of focussed pinholes 22. Each pinhole allows radiation emanating from the space V, from a volume in the shape of a cone, to pass and go to the detector 24. Three of these cones have been indicated in the FIG. 1. The pinholes 22 are focused towards a focus volume 31, which is here a relatively small part of the space V. Such focused pinholes 22 allow a lot of radiation and under many different angles to reach the detector 24, thus ensuring a high sensitivity and few artefacts.

Since the gamma camera 20, or preferably only the collimator 21 thereof with the detector in stationary position, can be moved in a scanning path by means of the motion device 26 in one or more of the orthogonal directions B1 and B2, even more imaging data can be obtained, in that the volume 31 is scanned through the breast 30.

The opening angle of the beams 23 may be selected or embodied by accordingly designing the pinholes 22. Additionally, and importantly, the absolute distance between the pinholes 22 and the volume 31, or generally e.g. the object 30, is very small. This allows a high magnification, a high sensitivity and with very good resolution.

In reality, the number of pinholes 22 of the first plurality of pinholes, in the upper collimator 12 will be larger than the three shown by way of example, such as a dozen pinholes 22. Nevertheless, for clarity, only three are shown here.

Importantly for understanding the present invention, in this prior art apparatus, the pinholes 22 of the collimator 21 are positioned symmetrically in the collimator when seen in this coronal view, so symmetrical with respect to the plane P, that is perpendicular to the collimator 21, parallel to the intended breast insertion direction B and passes through the geometrical centre C of the volume 31. With such a set of pinholes 22, the range of angles is from $-b_1$ to $+b_1$.

The opposite gamma camera 20, at the bottom side of the FIG. 1, has the exact same angular range, and thus adds no angular information, only sensitivity. Note that, for clarity reasons, the pinholes, acceptance angles etcetera, of the lower gamma camera 20 have not been indicated separately, but are of course mirror symmetrical with respect to the first, upper gamma camera. In FIG. 1, b1 is approximately 30°. Note that the angle between the central line of the leftmost pinhole and the perpendicular to this pinhole is slightly smaller.

Note the distance d2 between the plate 12 and the collimator plate 21. d2 may be made very small, such as 3 cm or smaller. In practice, it suffices if the collimator plate 21 can move parallel to plate 12 without too much friction, so theoretically the distance d2 could be as small as substantially zero.

Figure 2:
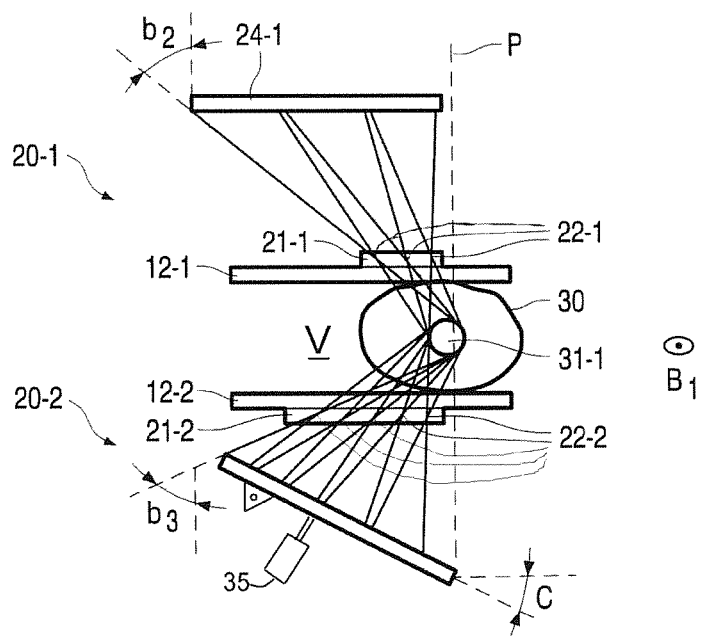
FIG. 2 diagrammatically shows an embodiment of the apparatus according to the invention, FIG. 3 diagrammatically shows another embodiment of the apparatus according to the invention, in a side elevational view.

FIG. 2 very diagrammatically shows—in coronal view—an embodiment of the apparatus according to the invention. Herein, as in all of the drawings, similar parts are indicated by the same reference numerals, if necessary provided with a suffix such as "-1", a prime "'", and so on. Again, parts not shown here but present in FIG. 1 may be provided in this embodiment.

In the apparatus of FIG. 2 a breast 30 is imaged, after inserting it along the practical breast insertion direction indicated by $B_1$ into the imaging space V between the pair of parallel breast positioning plates 12-1, 12-2. As is preferred adjustment of the spacing between the plates 12-1,12-2 is provided for in the frame of the apparatus. As is practically simple the plates 12-1,12-2 could be in horizontal orientation, but one may also envisage a support of the plates 12 to allow for a rotation of the pair of plates 12 about a horizontal axis perpendicular to a coronal plane of the subject, each so as to achieve an inclined orientation from the armpit downward similar to FIG. 6.

The gamma camera 20-1 has a detector 24-1 and a planar collimator plate part 21-1 with a first plurality of pinholes 22-1 focused onto a volume 31-1. Both the detector 24-1 and the camera height, i.e. the perpendicular distance between collimator 21-1 and the detector 24-1, are taken—for illustrative purposes only—to be of a similar size as in FIG. 1, thus giving a similar magnification factor. The first plane P is also indicated. As can be seen, the range of angles imaged by the pinholes 22-1 is now asymmetrical with respect to said plane P, as is the position of the total field of view, composed of the individual fields of view of the pinholes 22-1. The angle ranges in magnitude from zero to $b_2$. Clearly, $b_2$ is larger than $b_1$ in prior art FIG. 1. This opens up the possibility that more angular information is obtained with the same detector surface area. Here, b2 is approximately 52°. Furthermore, having the focus volume 31-1 generally to the side of the collimator 21-1, compared to the central location relative to the collimator as shown in FIG. 1, allows more freedom around that focus volume, e.g. for manipulating the breast or to gain access to the breast, e.g. for other equipment, the operator, etc.

The second gamma camera 20-2 has a second detector 24-2, here illustrated as of similar size as detector 24-1, as well as a collimator plate part 21-2 with a second plurality of focussed pinholes 22-2 focused onto focus volume 31-1.

Whereas in the camera 20-1 the detector 24-1 is parallel to the collimator plate part 21-1, the detector 24-2 is illustrated herein by way of example as being arranged in a tilted orientation, here a fixed angle tilted orientation, with respect to the collimator plate 21-1 over an angle C. This has as an effect that the range of angles for the imaging of volume 31-1 with the second plurality of pinholes 22-2 is now from zero to $b_3$, which is again larger than $b_2$. Note that the magnification factor varies over the detector 24-2, but this can be corrected for mathematically in the image processing software running on the image processing device of the apparatus. The FIG. 2 also reflects that in addition to the tilted or inclined orientation of the detector 24-2 also the number of pinholes 22-2 for imaging has increased compared to the arrangement in the camera 20-1. More important is that the range of angles is now much larger, here up to approximately 67°.

The detector 24-2 may be tiltable at variable tilt angles relative to the collimator 21-2 by means of detector tilting device 35 to set or adjust a tilting angle relative to the first collimator plate part.

Now, the total range of angles is from $-b_3$ to $+b_2$, which is approximately 120°, and much larger than from $-b_1$ to $+b_1$, which is only about 60°. Thereby, a much more precise imaging become possible.

The exemplary volume 31-1 may not always be the most useful of regions, or the most comfortable for the patient. However, it is to be stressed that allowing a non-symmetrical set-up for the plurality of pinholes 22-1, 22-2 allows the focus volume 31-1 to be positioned beyond its associated collimator 21-1, 22-1. Clearly, volume 31-1 extends beyond collimator 21-1. The freedom to position the focus volume within a patient has become greater with the set-up according to the present invention, as roughly the symmetrical second half of a collimator can be left out now.

Figure 3:
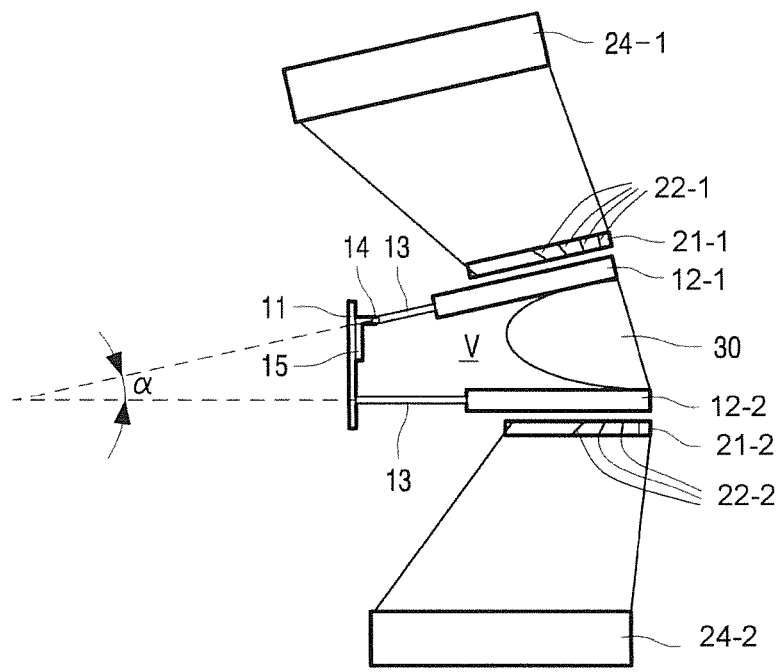

FIG. 3 diagrammatically shows another embodiment of the apparatus according to the invention, in a side elevational view so showing the breast 30 from the side and not in coronal or frontal view as in FIGS. 1 and 2.

Herein, a breast 30 is contacted by two positioning plates 12, that are each connected to the frame 11 by means of a respective connector member 13. One of the connections 13 has e.g. a hinge 14 or the like to position the two plates 12 in a V-shape, with an adjustable subtended angle α there between to obtain a variable tapering shape of the space between the plates 12 towards the front end of the breast 30.

A breast positioning plate motion device 15 is provided for adjusting the distance between the plates 12, in dependence of the breast size or the like. In practice, the angle α can be selected such that the plates 12 contact the breast 30 efficiently and as comfortable as possible, i.e. by minimizing overcompression, especially at the proximal end of the breast.

FIG. 3 furthermore illustrates the pinholes 22-1, 22-2 in collimators 21-1, 21-2, each adjacent a corresponding plate 12 at the side remote from the space V. These pinholes 22 are here only indicated by the directions of their respective centrelines. The pinholes 22-1, 22-2 in each collimator 21-1, 21-2 are provided close to the proximal end of the breast, and/or the centrelines of the pinholes 22-1, 22-2 are angled so as to be directed towards said proximal end of the breast 30. This allows efficient scanning of as much breast tissue as possible.

If the thickness of the breast tissue is locally larger, as here due to the tapering shape of the space V but also possible with parallel plates 12, the scanning time of said thicker region may be increased relative to the scanning time for a thinner region, e.g. by adjusting the zig-zagging pattern of the collimator 21 or of the entire camera over the plate 12 accordingly. Note that, although the asymmetry of the pinholes as seen in a vertical plane perpendicular to the paper does not show here, the added effects of the focus volume being positioned to the right in the FIG. 3, i.e. the increase of volume of imageable breast tissue by being able to image closer to the chest, as well as the increase in angular information according to the invention allows a much more accurate and reliable imaging.

Moreover, the collimators 21-1, 21-2, which can when desired be moved over the plates 12, e.g. in orthogonal directions, preferably in stepwise manner—by means of non-shown collimator motion device, e.g, with an electric motor drive, allowing scans of the breast 30, thereby allowing a film or dynamic imaging of the breast, since in principle only the collimator 12 is moved, in one plane. It could be useful to provide an oversized detector 24 in such a case when only the collimator 12 is moved and the detector held stationary during such a scan, or quick scan.

Figure 4:
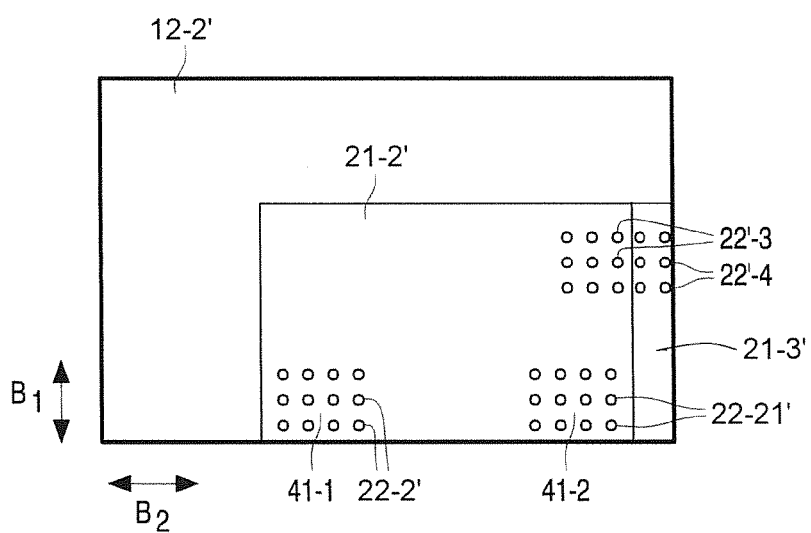
FIG. 4 is a diagrammatical top view of a detail of a lower gamma camera of another embodiment of the apparatus according to the invention, FIGS. 5A and 5B diagrammatically show a cross-sectional view in the coronal plane through embodiments of the apparatus of the invention, FIG. 6 diagrammatically shows a front view of an embodiment of the apparatus of the invention in use.

FIG. 4 is a diagrammatical top view of a detail of a gamma camera of another embodiment of the apparatus according to the invention.

The gamma radiation transparent and, preferably also optical transparent, first positioning plate part 12' can be seen, below which is positioned the collimator 21' embodied as a rectangular collimator plate and provided with a first plurality of pinholes 22'-2 in a first corner 41-1 and a second plurality of pinholes 22'-21' in a second corner 41-2 of the collimator plate.

FIG. 4 also illustrates the presence of a second collimator plate part 21-3' adjoining the first plate part 21-2' along an edge thereof and extending at a non-zero angle, here perpendicular, relative to said first plate part 21-2' of the collimator. One or more additional sets of multiple pinholes 22'-3 and 22'-4 are provided in plate parts 21-2' and 21-3' respectively.

In use, a first breast, in particular the right breast, may be imaged in the first corner 41-1, by the first pinholes 22'-1. Thereto, it is inserted along arrow B1, from the bottom side of the page. Subsequently, the breast may be imaged by moving the gamma camera or the collimator plate part 21' along the plate 12', in the directions of the arrows B1 and/or B2. Moreover, a second breast, in particular the left breast, may be imaged in the second corner 41-2 by the second plurality of pinholes 22'-2. Thereto, the breast is inserted in the direction of the arrow B1 from the bottom of the page, again moving the gamma camera or collimator plate part 21' in the direction of the arrows B1 and/or B2. This set-up is symmetrical as to scanning, while allowing great freedom of movement for the patient.

Figure 5A:
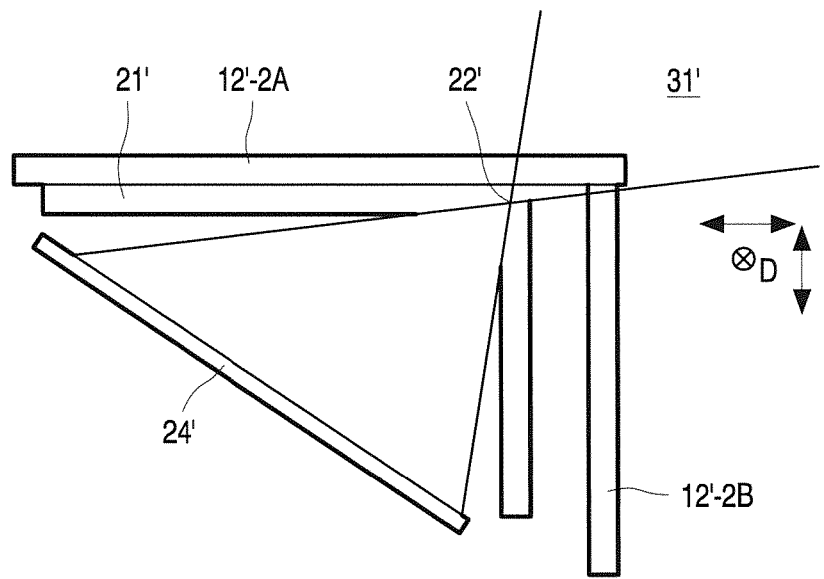
Figure 5B:
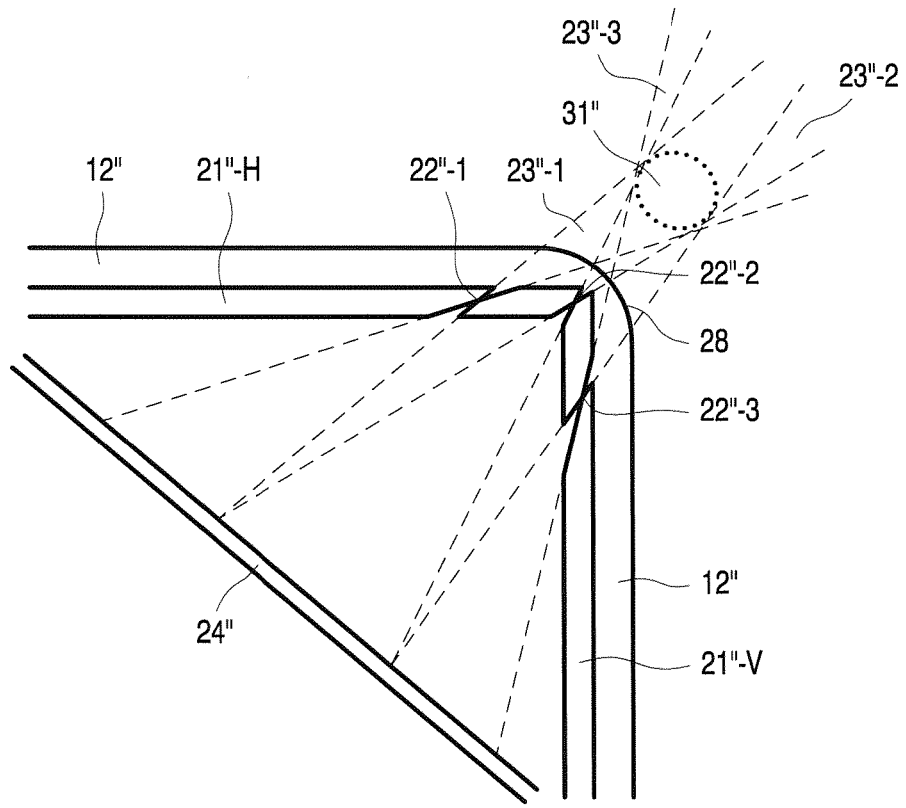
Figure 6:
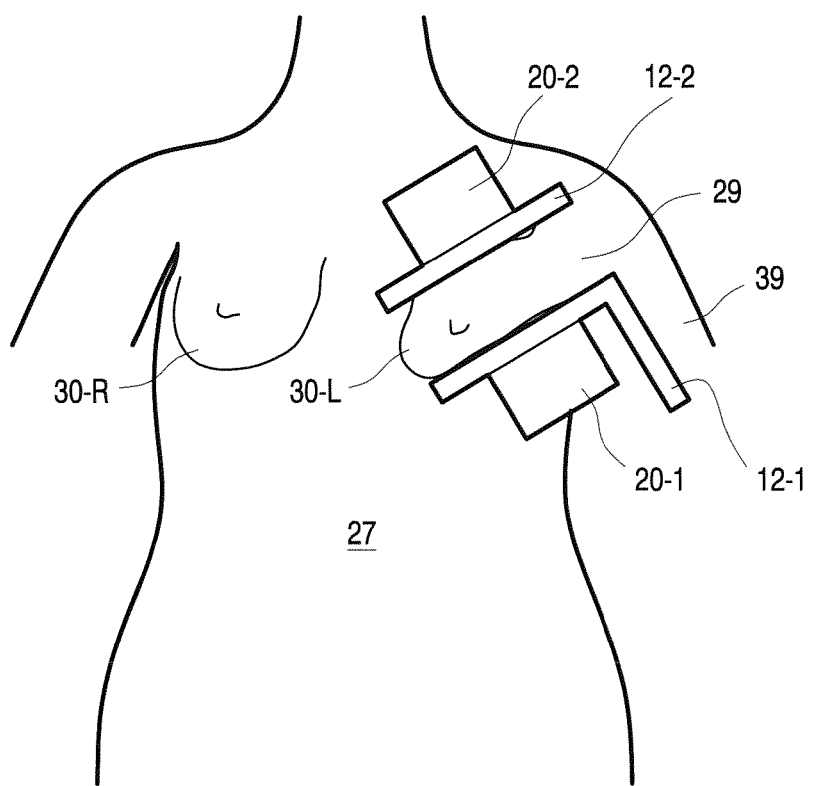

The additional pluralities of pinholes 22'-3 and/or 22'-4 can be used for imaging additional tissue, in particular of an armpit, as will be elucidated further in connection with FIGS. 5 and 6. Here, it is remarked that a subject may insert his/her arm, from the right, in the direction along arrow $B_2$, such that the tissue can be imaged by the pinholes 22'-3 and 22'-4.

FIGS. 5A and 5B diagrammatically show a cross-sectional view in the coronal plane through embodiments of the apparatus of the invention, with emphasis on the possibility for axillary imaging.

FIG. 5A shows a very simple embodiment, in which there is only one pinhole 22' for axillary imaging per coronal plane, provided at the very edge of the collimator 21', here embodied with two perpendicular plate parts adjoin at said very edge. Said one pinhole 22' has a field of view 31' with an acceptance angle. Compare this to the 3×5 set of pinholes in FIG. 4. Nevertheless, the set-up is still very useful, as will be shown in more detail in relation to FIG. 6. In FIG. 5A itself, it is to be understood that the collimator 21', which will also comprise a non-shown asymmetrical set-up of a first plurality of pinholes for breast imaging, can be moved along the three orthogonal directions indicated with the arrows at D, i.e. along the mutually moveable horizontal plate part 12'-2A and the vertical plate part 12'-2B, as well as along the direction into and out of the plane of the drawing. This will allow full scanning of the tissue from the breast to the armpit. Note that any upper part of the second gamma camera, as visible in FIG. 2, would be less useful here due to the larger distance, and is thus omitted. For convenience, the detector 24' has been shown tilted, but it could also have been provided parallel to one of the collimator 21' or plate parts 12'-2A/B.

FIG. 5B shows another embodiment, with three pinholes 22"-1/2/3 in the or each coronal plane, having respective fields of view (acceptance angles) 23"-1/2/3, and together forming the common or central field of view 31" distinct from a non-shown field of view offered by a first plurality of pinholes for breast imaging. Note that, especially for low pinhole numbers, this would effectively be the angular, multi-faceted volume covered by all pinhole fields of view. For convenience only, it is taken here to be a circle/sphere. Again, there is a pinhole 22"-2 on the very edge of the two plate-parts collimator, with one pinhole in each plate part of the collimator 21"-H and 21"-V. For ease of use, the plates 12" that from the positioning member form a sharp edge at the side of the collimator, but a rounded-off edge 28 at the side or apex where a subject would position her arm or armpit. This allows a more comfortable position for the subject, while allowing a straight path and close distance for the collimator/detector when it moves along the plate parts 12" for imaging the subject's axillary and breast tissue. To do so, the subject could e.g. position her arm on top of the plate 12" part that is parallel to the collimator part 12"-H, while the torso would be substantially parallel to the "vertical" part parallel to collimator part 21"-V. The gamma camera comprising the collimator 21"-H/V and the detector 24" could then be moved parallel to the plate 12", both horizontally and into/out of the paper until it reaches the edge near 28, and then downwards and out of/into the paper. Again, in this way a full scan can be obtained.

FIG. 6 diagrammatically shows a frontal view of a subject and of an embodiment of the apparatus of the invention in use. The embodiment shown comprises two gamma cameras 20-1 and 20-2 and respective positioning members 12-1 and 12-2. Herein, as is preferred, the plate 12-2 is embodied as a singular planar plate and member 12-1 is embodied with two perpendicularly joined plate parts in order to position the breast from the outer side as well as a portion of the arm of the subject in the region of the armpit.

The gamma cameras 20-1, 20-2, at least the collimators thereof, are movable along the plate 12-1 and the plate parts of member 12-2 respectively to scan the breast and the axillary region.

The assembly of positioning members 12-1, 12-2 and gamma cameras 20-1, 20-2 is shown—when seen in frontal view—to be tilted over an angle of about 45° with respect to the horizontal. In the drawing, the left breast 30-L of the subject 27 is being imaged, as well as axillary tissue 29 of the arm 39. The right breast 30-R is not being imaged, but one can envisage a mobile support of the assembly relative to the frame of the apparatus so that also the right breast can be imaged in similar fashion. This possibility can also be offered for an embodiment wherein both plate members 12-1, 12-2 are singular plates, so without the provision of an additional plate part that engages the arm near the armpit as shown here.

In the depicted embodiment advantages of the invention can be seen in that a large part of said axillary tissue can at all be imaged, because the focus volume is far outside the centre of the cameras 20. It can furthermore be imaged with a lot (more) of angular information. It can also be scanned at the same time that the main body of the breast itself is scanned, or at least if desired so.

A possible order of use could be to scan the left breast 30-L with both gamma cameras 20-1 and 20-2 in place with the breast compressed between the plates 12-1 and 12-2, all in a substantially horizontal position, followed by tilting the cameras and members 12-1, 12-2 over substantially 45°, as shown in FIG. 6, either then imaging both the breast and axillary tissue in a compressed state, with the arm 39 of the subject 27 positioned as shown, or the upper gamma camera 20-2 including the plate 12-2 being moved away from the breast. In either case, the lower camera 20-1 can scan the tissue by moving along both parts of plate 12-1. A big advantage may be the more comfortable posture for the subject 27, and of course the completeness of the scan, noting that it is often the (lymphe part of the) axillary tissue that is most relevant for these types of scans.

Figure 7:
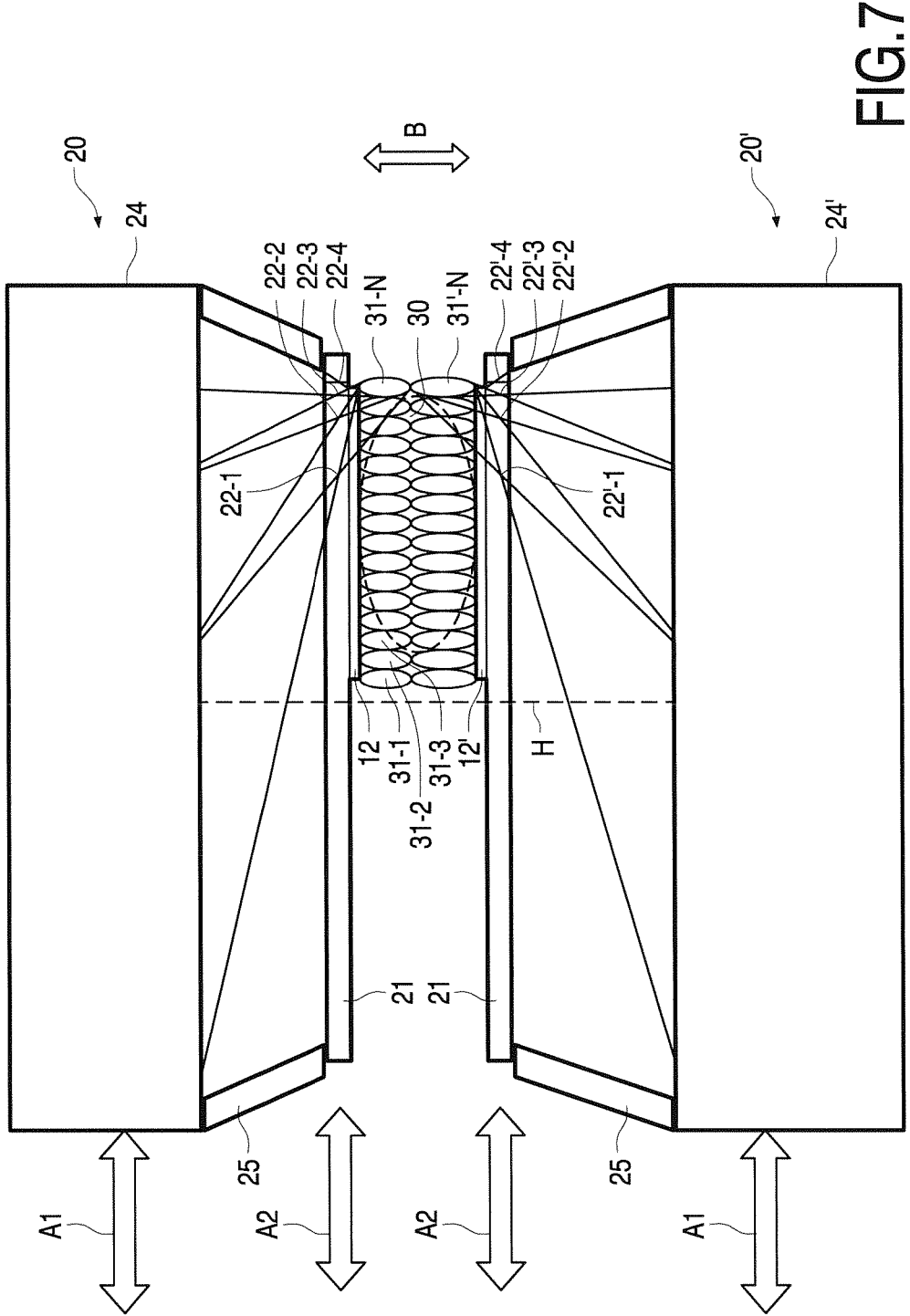
FIG. 7 shows yet another embodiment of the invention, in a schematical front view.

FIG. 7 shows yet another embodiment of the invention, in a schematical frontal view on the apparatus and the subjects breast. The view is on the coronal plane of the subject and breast. The breast 30 that is being imaged here is the right breast of a subject.

A large number of central fields of view 31-1, 31-2, 31-3, . . . are visible. These arise in the use of the apparatus as follows. In the position of the apparatus as shown, the pinholes 22-1, . . . of the upper collimator 21 have a common field of view that has been indicated schematically as 31-N. Similarly, the pinholes 22'-1, 22'-2, . . . of the lower collimator 21' have a common field of view 31'-N. Note that the CFOV 31-N and 31'-N do not overlap, which is due in this case to the relatively large thickness of the breast 30. This is however no problem if the image reconstruction is adapted accordingly. In this situation, the first image is collected.

Next, the cameras 20 and 21' will be moved or shifted, in this case to the left, i.e. in the direction of arrows A1/A2, such that in the next position the next CFOVs are imaged, and so on, e.g. until the images/CFOVs 31-3, 31-2 and 31-1 are imaged, as well as their counterparts for the lower collimator (not indicated separately). Note that it is also possible, e.g. by adapting the collimators 21 and 21', or the shielding housings 25 and 25', to move only the collimators 21 and 21', along the directions indicated by arrows A2, in order to shift the CFOVs. Since shifting only the collimator plates, that are a lot lighter than the detectors and housings 24(') and 25(') weighing up to hundreds of kilograms, is much easier, imaging can be performed faster, which is more comfortable for the patient, and also more accurate.

It is also possible to combine the two movements, in that in a first position of the detectors/housings a first (smaller) number of images are taken, followed by a shifting of those detectors/housing, in turn followed by again a number of images for different collimator positions, and so on. It is to be noted that the field of view for pinhole 22-4 has not been indicated in the drawing. This is done e.g. because the corresponding portion of the detector is non-sensitive, or because it is effectively shielded by the housing 25. After a shift of the collimator 21, the pinhole 22-4 may become effective in imaging, e.g. at the cost of (part of) the image of pinhole 22-1.

Figure 8:
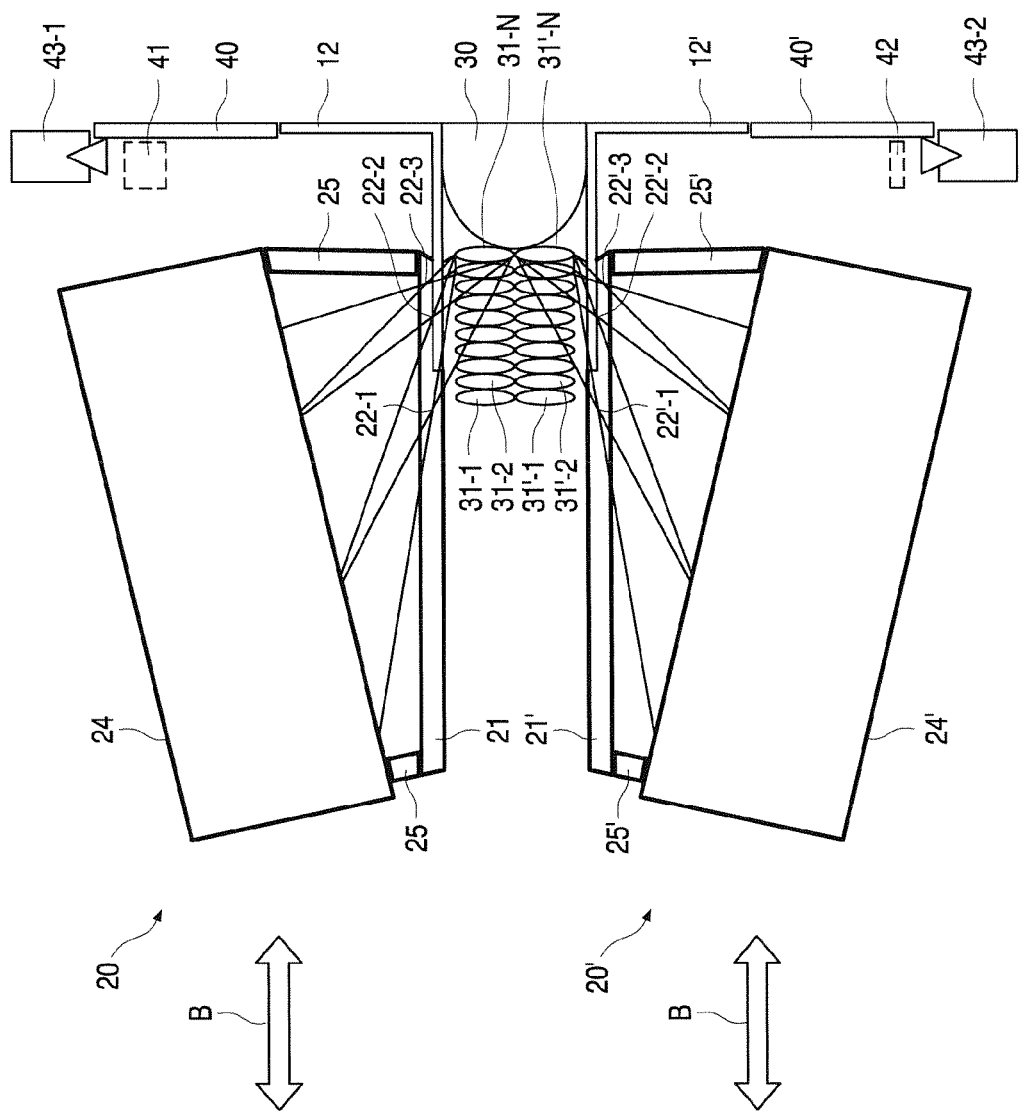
FIG. 8 shows yet another embodiment, in a diagrammatical view on the sagittal plane, FIG. 9 diagrammatically shows the embodiment of FIG. 8, in a different position.

FIG. 8 shows yet another embodiment, in a diagrammatical view on the sagittal plane, i.e. with the intended insertion direction of the breast 30 in the plane of the paper.

In addition to the parts already mentioned, this embodiment further comprises an outer housing 40/40' and one or more, here two, optical cameras 43-1 and 43-2, as well as optionally an X-ray source 41 and an X-ray detector 42.

The optical cameras 43-1 and 43-2 help the operator to position the focus of the cameras 20 and 20', in that they provide an optical image for guidance.

Additionally or alternatively, there may be provided an X-ray source 41 and an X-ray detector 42, for similar reasons. Note that it is possible to provide both types of "guidance support means" (optical and X-ray) when suitable angled and/or when at least one of these is provided (re)moveably.

Furthermore, in the embodiment and position shown, the pinholes 22-1, 22-2, . . . of the upper collimator are also provided asymmetrically, now in the sagittal plane. Together, the pinholes define a CFOV that has been indicated schematically by 31-N, while their counterparts 22'-1, 22'-2, . . . define a CFOV that has been indicated schematically by 31'-N. After taking these images, the collimators 21/21' are moved along the direction of arrows B away from the torso of the subject, for taking subsequent images up to CFOVs 31-2/31'-2 and finally 31-1/31'-1. Of course, in the instance shown, all the CFOVs are outside the breast 30, so do not make much sense. But if the breast 30 would be larger, i.e. extend further into the camera 20/20', there would be relevant images. Nevertheless, the possibility is clear. As a next step in imaging, the cameras 20/20' as a whole, or possibly only the collimators 21/21' are moved, over a larger step and in the direction of arrows B, towards the subject. This is shown in FIG. 9.

Figure 9:
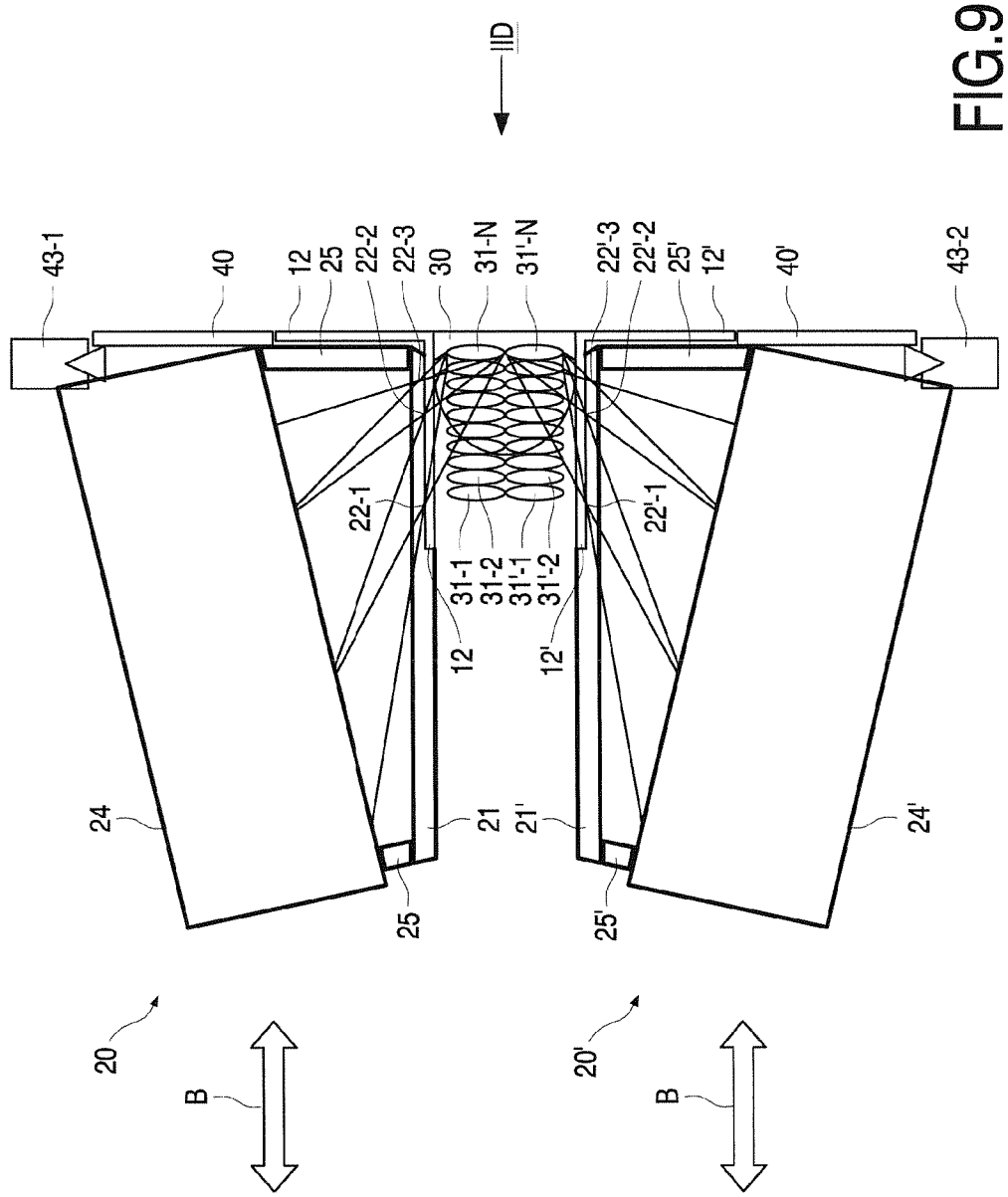

FIG. 9 diagrammatically shows the embodiment of FIG. 8, in a different position.

In particular, the cameras 20 and 20' have been moved toward the chest of the subject (of which only the breast 30 is shown) as much as possible, along the direction of B, which corresponds in this case to the intended insertion direction IID. In this situation, the pinholes 22-1, 22-2 of the upper collimator have a CFOV indicated by 31-N, and their counterparts 22'-1, 22'-2, . . . of the lower collimator 21' have a CFOV indicated by 31'-N. By shifting the collimators 21/21' along the direction of arrows B away from the subject, more and more CFOVs are imaged, up until 31-2/31'-2 and 31-1/31'-1, or correspondingly fewer if stopped until no longer relevant for no longer imaging breast tissue. It can be seen that the present invention can not only image more accurately, because it provides more angular information, but also because a very large part of the breast tissue can be imaged, and also more comfortably.

It is to be noted that the moveability in A1/A2 and B of FIGS. 7-9 can be, and preferably is, present in the embodiments shown.

Figure 10:
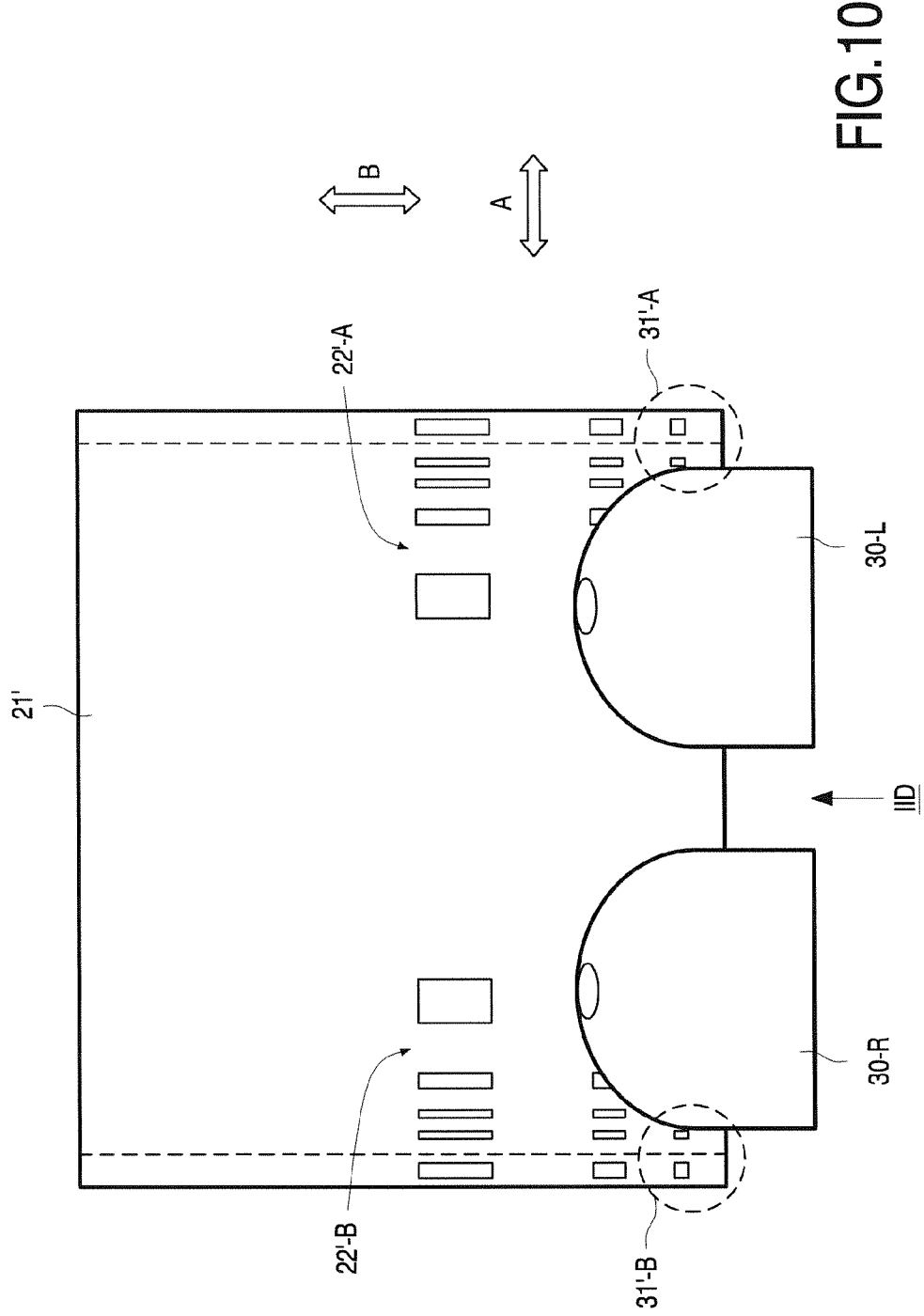
FIG. 10 is a diagrammatic top view onto the lower collimator 21' of e.g.

FIG. 10 is a diagrammatic top view onto the lower collimator 21' of e.g. FIGS. 7-9, in use for the two different positions for the left and right breast. Note that, although both breasts are shown, it is not intended for them to be imaged simultaneously, and that the breast shown to the left in the drawing is actually the right breast of a subject, and vice versa.

For the left breast 30-L, inserted along the intended insertion direction IID, a first plurality of pinholes 22'-A provide a first focus volume or CFOV indicated diagrammatically by dashed circle 31'-A. By moving the collimator 21' in the directions indicated by arrows A and B, this focus volume 31'-A can be moved through the left breast 30-L to image it completely. In this situation, the right breast would be to the right of the camera, outside the compressing plates.

When the right breast 30-R is to be imaged, it is positioned as indicated, in the corner where a second plurality of pinholes 22'-B is situated, that have a focus volume or CFOV 31'-B. Again, by shifting the collimator 21' along arrows A and/or B, the right breast 30-B can be imaged completely. In this case, the left breast would also be positioned outside the camera, for less discomfort.

The specific embodiments shown here and their features may be combined in any desired way, unless specifically described to the contrary. Furthermore, the embodiments shown are to be understood merely as a non-limiting explanation of the invention, whose scope is defined by the appended claims.

What is claimed is:

1. A gamma radiation breast imaging apparatus, said apparatus comprising: a breast positioning device, which comprises a frame supporting a pair of breast positioning plates defining between them an imaging space for a breast to be imaged of a subject, wherein at least one of the breast positioning plates is movably mounted to said frame in a first direction substantially towards the other breast positioning plate allowing the breast positioning plates to compress the breast when positioned between said breast positioning plates, said apparatus further comprising: a gamma camera positioned to image a volume in said imaging space, wherein the gamma camera comprises: a collimator having a first collimator plate part that is provided with at least a first plurality of focused pinholes, each of said first plurality of focused pinholes having an individual field of view, the individual fields of view of the first plurality of pinholes defining a common central field of view as the part of space seen by all of the first plurality of pinholes, and a gamma sensitive detector arranged to receive images from the collimator, wherein the first collimator plate part of the collimator is positioned in a plane substantially parallel and adjacent to one of the breast positioning plates and is movable in said plane whilst the breast is compressed between the breast positioning plates, and wherein the apparatus further comprises a collimator motion device arranged to controllably move the collimator in said plane whilst the breast is compressed between the breast positioning plates, wherein the first plurality of focused pinholes in said first collimator plate part is provided non-symmetrically when viewed in a coronal plane of the breast whilst the breast is compressed between the breast positioning plates.

2. The apparatus of claim 1, wherein the individual field of view of each pinhole of said first plurality of focused pinholes has a central line, wherein said first plurality of focused pinholes has a first pinhole of which the central line subtends a first angle with a perpendicular to the first collimator plate part which is the largest for said first plurality of focused pinholes, and a second pinhole that is furthest away from said first pinhole, wherein said first angle is substantially larger than a second angle between the central line of said second pinhole and a perpendicular to the first collimator plate part.

3. The apparatus of claim 2, wherein said first angle is at least 45°, preferably at least 60°, and wherein preferably said second angle is smaller than 30°.

4. The apparatus of claim 1, wherein the first collimator plate part is a rectangular collimator plate part of radiation opaque material, in which there is provided said first plurality of focused pinholes in a first corner of said first collimator plate.

5. The apparatus of claim 4, wherein the first collimator plate further comprises a second plurality of focused pinholes, and wherein the second plurality of focused pinholes is provided at a neighbouring corner to said first corner and is substantially a mirror image of said first plurality of focused pinholes.

6. The apparatus of claim 1, comprising two of said gamma cameras, each associated with one of said two breast positioning plates.

7. The apparatus of claim 1, wherein at least one breast positioning plate comprises a planar first breast positioning plate part, and is further provided with a second positioning plate part that adjoins the first breast positioning plate part and extends at a non-zero angle to said first breast positioning plate part.

8. The apparatus of claim 1, wherein the collimator associated with said at least one breast positioning plate and a corresponding collimator motion device are configured to move the first plate part of the collimator in a scanning path along said first breast positioning plate part and along said second positioning plate part.

9. The apparatus of claim 7, wherein the frame of the apparatus is embodied to support said breast positioning plate such that said first breast positioning plate part is oriented to support the breast laterally and the second positioning plate part is oriented to support a portion of the upper arm of the subject in the region of the armpit.

10. The apparatus of claim 9, wherein the frame of the apparatus is embodied to support said breast positioning plate such that—when seen in coronal view—the first breast positioning plate part is oriented at an incline from said armpit towards a center of the torso and the second positioning plate part is oriented at an incline from the armpit downward and outward.

11. The apparatus of claim 1, wherein the collimator comprises said a first collimator plate part and a second collimator plate part that adjoins the first collimator plate part and extends at a non-zero angle to said first collimator plate part.

12. The apparatus of claim 11, wherein said collimator comprises a third plurality of pinholes each of the pinholes of said third plurality of pinholes having an individual field of view, the individual fields of view of the third plurality of pinholes defining a common third central field of view as the part of space seen by all of the third plurality of pinholes, said third central field of view being distinct from said central field of view of said first plurality of focused pinholes and any second plurality of focused pinholes, said third central field of view corresponding to an armpit region of the subject.

13. The apparatus of claim 12, wherein the third plurality of pinholes is provided in the region where the second collimator plate part adjoins the first collimator plate part.

14. The apparatus of claim 11, wherein the first collimator plate part is parallel to the first positioning plate part and wherein the second collimator plate part is parallel to the second positioning plate part, preferably the adjoining plate parts extending perpendicular to one another.

15. The apparatus of claim 11, wherein at least one breast positioning plate comprises a planar first breast positioning plate part, and is further provided with a second positioning plate part that adjoins the first breast positioning plate part and extends perpendicular to said first breast positioning plate part, and wherein the collimator motion device is adapted to at least allow for displacement of the collimator along an axis perpendicular to the second positioning plate part with the first collimator plate part moving closely along the first breast positioning plate part, and to at least allow for displacement of the collimator along an axis perpendicular to the first breast positioning plate part with the second collimator plate part moving closely along the second positioning plate part.

16. The apparatus of claim 11, wherein the detector is arranged at an angle relative to both the first collimator plate part and the second collimator plate part.

17. The apparatus of claim 1, wherein the frame of the apparatus is embodied to support said pair of breast positioning plates such that—when seen in coronal view—said breast positioning plates are each oriented at an incline from an armpit of the subject down towards a center of the torso of the subject.

18. The apparatus of claim 17, wherein the frame is embodied to allow for displacement of the pair of breast positioning plates between such inclined orientation for the left-hand breast and such inclined orientation for the right-hand breast.

19. The apparatus of claim 1, wherein at least one optical camera is provided allowing an operator of the apparatus to obtain an optical view of the breast positioned between the breast positioning plates in the apparatus.

20. The apparatus of claim 1, wherein the apparatus is provided with an x-ray source and an X-ray radiation camera with a detector adapted for X-ray or a detector adapted for both gamma and X-ray radiation, so as to allow for dual mode operation of the apparatus.

21. A method for imaging a breast by means of a gamma radiation imaging apparatus according to claim 1, wherein the method comprises: insertion of the breast to be imaged in an intended insertion direction between the breast position plates, moving at least one of the breast positioning plates to compress the breast, operating the at least one gamma camera to obtain an image of the breast, wherein the collimator motion device is operated to controllably move the collimator with the first collimator plate part thereof in a plane substantially parallel to an adjacent breast positioning plate.

* * * * *